United States Patent
Yang

(10) Patent No.: US 11,077,065 B2
(45) Date of Patent: *Aug. 3, 2021

(54) PROCESS FOR PREPARING AN ACID RESISTANT CELLULOSE CAPSULE

(71) Applicant: SUHEUNG CO., LTD., Chungbuk (KR)

(72) Inventor: Joo-Hwan Yang, Gyeonggi-do (KR)

(73) Assignee: SUHEUNG CO., LTD., Chungbuk (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/793,179

(22) Filed: Feb. 18, 2020

(65) Prior Publication Data

US 2020/0281860 A1  Sep. 10, 2020

(30) Foreign Application Priority Data

Feb. 19, 2019  (KR) .......................... 10-2019-0019076

(51) Int. Cl.
| | |
|---|---|
| *A61K 9/48* | (2006.01) |
| *A61K 47/02* | (2006.01) |
| *A61K 47/12* | (2006.01) |
| *A61K 47/26* | (2006.01) |
| *A61K 47/34* | (2017.01) |
| *A61K 47/36* | (2006.01) |
| *A61K 47/38* | (2006.01) |

(52) U.S. Cl.
CPC ............ *A61K 9/4825* (2013.01); *A61K 47/02* (2013.01); *A61K 47/12* (2013.01); *A61K 47/26* (2013.01); *A61K 47/34* (2013.01); *A61K 47/36* (2013.01); *A61K 47/38* (2013.01)

(58) Field of Classification Search
None
See application file for complete search history.

(56) References Cited

U.S. PATENT DOCUMENTS

| | | |
|---|---|---|
| 6,410,050 B1 | 6/2002 | Yang |
| 2008/0134937 A1* | 6/2008 | Yang .................... C08L 1/28 106/162.9 |

FOREIGN PATENT DOCUMENTS

WO    2011036601 A1    3/2011

OTHER PUBLICATIONS

Al-Tabakha, M.M., "Performances of New Generation of Delayed Release Capsules", J. Young Pharmacists, vol. 7, No. 1 (2015) pp. 36-44.

* cited by examiner

*Primary Examiner* — Patricia Duffy
*Assistant Examiner* — Garen Gotfredson
(74) *Attorney, Agent, or Firm* — MH2 Technology Law Group, LLP

(57) ABSTRACT

A process for preparing an acid resistant cellulose capsule. An example of a process for preparing an acid resistant cellulose capsule includes the steps of: i) preparing 100 wt part of aqueous solution of solubilized cellulose including 15-25 wt part of cellulose; ii) sequentially adding and solubilizing: 2.0-4.0 wt part of amid pectin and 0.1-1.0 wt part of iota-carrageenan as a gelling agent, an auxiliary gelling agent, a pH neutralizing agent, an emulsifying agent, a viscosity stabilizing agent and a plasticizing agent to the resulting admixture; and iii) allowing it to stand and to be equilibrated with adjustment of viscosity, before forming the capsule.

6 Claims, 2 Drawing Sheets

PROCESS FOR PREPARING AN ACID RESISTANT CELLULOSE CAPSULE

CROSS-REFERENCE TO RELATED APPLICATIONS

This application claims priority to Korean Application No. 10-2019-0019076 filed on 19 Feb. 2019, the entire disclosure of which is hereby incorporated by reference in its entirety.

TECHNICAL FIELD

The present invention relates to a process for preparing an acid resistant cellulose capsule. More specifically, this invention relates to a process for preparing an acid resistant cellulose capsule comprising the steps of: i) preparing 100 wt part of aqueous solution of solubilized cellulose including 15-25 wt part of cellulose; ii) sequentially adding and solubilizing 2.0-4.0 wt part of amid pectin and 0.1-1.0 wt part of iota-carrageenan as a gelling agent, an auxiliary gelling agent, a pH neutralizing agent, an emulsifying agent, a viscosity stabilizing agent and a plasticizing agent to the resulting admixture; and iii) allowing it to stand and to be equilibrated with adjustment of viscosity, before forming the capsule.

DESCRIPTION OF PRIOR ART

Gelatin hard capsule using animal protein has been conventionally used and commercialized. Recently, it has been found that a gelatin hard capsule can be denaturalized by the degradation of protein. Further, gelatin hard capsule can have a handicap for filling a hygroscopic and/or a moisture sensitive preparation due to its high water content (11-16 wt %). Accordingly, a cellulose hard capsule especially using hydroxypropyl methyl cellulose (HPMC) as base material has been replacing the gelatin hard capsule due to its relatively low water content (3-6 wt %).

A cellulose hard capsule has been also disclosed in U.S. Pat. No. 6,410,050 'Cellulose capsule using mixed solution of pectin and glycerin and the manufacturing process thereof', which is inventor's own patent publication. In this patent publication, a cellulose hard capsule prepared by the steps comprising: i) preparing a mixed solution of pectin and glycerin, ii) adding said mixed solution to solubilized cellulose aqueous solution, iii) adding a small amount of glacial acetic acid, calcium gluconate, sucrose fatty acid ester to said mixture, and iv) standing by adjusting viscosity and forming a capsule has been disclosed.

On the other hand, it has been also disclosed that the gelling agent, such as, carrageenan, sodium alginate, gellan gum and/or pectin can be used as gelling agent for cellulose hard capsule. If gelling agent is combined with metal cations, such as, potassium, calcium and/or sodium cation, the gelling properties can be far enhanced.

Further, it has been reported that an enteric film coating or imparting the acid resistance to the cellulose hard capsule can result in the increase of bioavailability of core drug, because the absorption and/or metabolism of core drug can be delayed.

For absorbing the core drug in the intestine, an enteric film coating has been already disclosed. As enteric film coating agent, an acid resistant material having pH-dependent dissolution profile can be used. For this purpose, cellulose acetate phthalate (CAP), hydroxypropyl methyl cellulose phthalate (HPMCP), hydroxypropyl methyl cellulose acetate succinate (HPMC-AS), acrylate copolymer and/or polymer containing carboxylate such as shellac can be applied.

Further, an acid resistant capsule imparting the acid resistance to the cellulose hard capsule has been already developed. In WO 2011/036601 'Acid resistant capsules', an acid resistant capsule comprising (i) an aqueous solvent, (ii) gellan gum, and (iii) one or more water soluble film forming polymers has been disclosed. Further, it has been disclosed that the weight ratio of gellan gum to said one or more water soluble film forming polymers is between 4/100 to 15/100, wherein said water soluble film forming polymer is preferably hydroxypropyl methyl cellulose (HPMC).

According to the article 'Performances of New Generation of Delayed Release Capsules' by Moawia Al-Tabakha et al., it has been reported that the new generation of capsules designed to protect the ingredient from the acid environment of stomach have not performed in such a manner as to comply with the USP requirements for disintegration and dissolution of delayed-release dosage form (Moawia M. Al-Tabakha et al., Journal of Young Pharmacists, Vol. 7, Issue 1, January-March 2015).

For imparting the acid resistance to the cellulose capsule, the inventor of present application has increased the amount of amide pectin with iota-carrageenan as a gelling agent compared to commercially marketed cellulose capsule disclosed in U.S. Pat. No. 6,410,050. Further, an acid resistant cellulose capsule of the present invention has been developed by adding potassium carbonate ($K_2CO_3$) and calcium gluconate as an auxiliary gelling agent for improving the film strength of cellulose capsule, a colloidal silica as a viscosity stabilizing agent for maintaining the proper viscosity of cellulose aqueous solution, and glycerin, PEG 4000 and/or propylene glycol as a plasticizing agent for maintaining the plasticity of film.

Problem to be Solved

The problem to be solved is to develop an acid resistant cellulose capsule by increasing the amount of amide pectin with iota-carrageenan as a gelling agent compared to commercially marketed cellulose capsule disclosed in U.S. Pat. No. 6,410,050. Further, an acid resistant cellulose capsule has been developed by adding potassium carbonate ($K_2CO_3$) and calcium gluconate as an auxiliary gelling agent for improving the film strength of cellulose capsule, a colloidal silica as a viscosity stabilizing agent for maintaining the proper viscosity of cellulose aqueous solution, and glycerin, PEG 4000 and/or propylene glycol as a plasticizing agent for maintaining the plasticity of film.

Means for Solving the Problem

The object of present invention is to provide a process for preparing an acid resistant cellulose capsule comprising the steps of i) preparing 100 wt part of aqueous solution of solubilized cellulose including 15-25 wt part of cellulose; ii) adding and stirring 2.0-4.0 wt part of amide pectin and 0.1-1.0 wt part of iota-carrageenan as a gelling agent, and 0.01-0.2 wt part of potassium carbonate and 0.01-0.2 wt part of calcium gluconate as an auxiliary gelling agent to the aqueous solution of solubilized cellulose; iii) sequentially adding and stirring 0.01-0.1 wt part of glacial acetic acid as a pH neutralizing agent, 0.01-0.2 wt part of sucrose fatty acid ester and diacetylated monoglyceride as an emulsifying agent, 0.01-0.1 wt part of colloidal silica as a viscosity stabilizing agent, and 0.01-0.1 wt part of glycerin, PEG 4000 and/or propylene glycol as a plasticizing agent to the resulting admixture; and iv) allowing obtained product to stand and to be equilibrated with adjustment of its viscosity, and forming and drying a cellulose capsule.

Further, in said step iv), a cellulose aqueous mixture obtained in step iii) stands at 65° C. and dipping the molding pin, forming a cellulose capsule, and drying it at 30-37° C.

Further, the said cellulose is hydroxyl propyl methyl cellulose (HPMC 2910) and the said amide pectin is low methoxyl amide pectin.

Further, said colloidal silica is stable spherical particle having 5-8 wt % of SiO2 content, pH 10-12 with 2-5 nm of particle size.

Another object of present invent ion is to provide an acid resistant cellulose capsule, wherein the bioavailability of ingredient drug shows at least 5% increase of Area Under Curve (AUC) compared to that of currently marketed cellulose capsule.

The further object of present invention is to provide an acid resistant cellulose capsule, wherein the dissolution profile shows 8-12 wt % of dissolution of the contents for 120 minutes in the first solution (pH 1.2) and 95-100 wt % of subsequent dissolution of the contents for next 120 minutes in the second solution (pH 6.8), according to the paddle method of the dissolution test in the Korean pharmacopoeia 10th Edition.

Advantageous Effect

The outstanding advantageous effect of the present invention is to provide an acid resistant cellulose capsule by increasing the amount of amide pectin with iota-carrageenan as a gelling agent. Further, an acid resistant cellulose capsule containing potassium carbonate (K$_2$CO$_3$) and calcium gluconate as an auxiliary gelling agent for improving the film strength, a colloidal silica as a viscosity stabilizing agent for maintaining the proper viscosity of cellulose aqueous solution has been provided.

PREFERRED EMBODIMENT OF INVENTION

Figure 1:
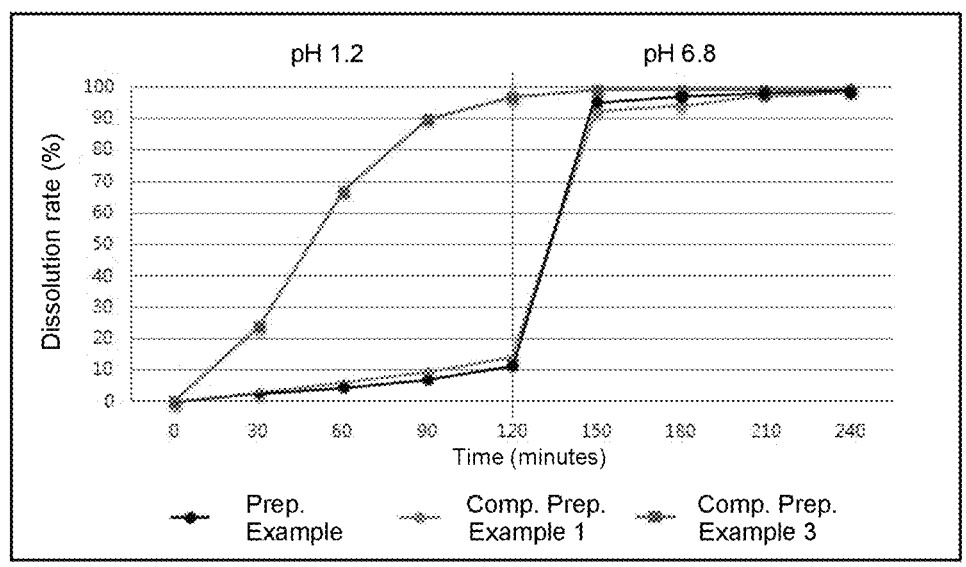
FIG. 1 shows a dissolution profile of acetaminophen by the acid resistant cellulose capsule of the present invention (Preparation Exp), and the cellulose capsule EMBO CAPS VG commercially marketed by Suheung Co., Ltd. (Comparative Preparation Exp 3), according to the paddle method of the dissolution test in the Korean pharmacopoeia 10th Edition.

The present invention relates to a process for preparing an acid resistant cellulose capsule comprising the steps of i) preparing 100 wt part of aqueous solution of solubilized cellulose including 15-25 wt part of cellulose; ii) adding and stirring 2.0-4.0 wt part of amide pectin and 0.1-1.0 wt part of iota-carrageenan as a gelling agent, and 0.01-0.2 wt part of potassium carbonate and 0.01-0.2 wt part of calcium gluconate as an auxiliary gelling agent to the aqueous solution of solubilized cellulose; iii) sequentially adding and stirring 0.01-0.1 wt part of glacial acetic acid as a pH neutralizing agent, 0.01-0.2 wt part of sucrose fatty acid ester and diacetylated monoglyceride as an emulsifying agent, 0.01-0.1 wt part of colloidal silica as a viscosity stabilizing agent, and 0.01-0.1 wt part of glycerin, PEG 4000 and/or propylene glycol as a plasticizing agent to the resulting admixture; and iv) allowing obtained product to stand and to be equilibrated with adjustment of its viscosity, and forming and drying a cellulose capsule.

Further, in said step iv), a cellulose aqueous mixture obtained in step iii) stands at 65° C. and dipping the molding pin, forming a cellulose capsule, and drying it at 30-37° C.

Further, the present invention also relates to an acid resistant cellulose capsule, wherein the bioavailability of ingredient drug shows at least 5% increase of Area Under Curve (AUC) compared to that of currently marketed cellulose capsule.

Further, the present invention also relates to an acid resistant cellulose capsule, wherein the dissolution profile shows 8-12 wt % of dissolution of the contents for 120 minutes in the first solution (pH 1.2) and 95-100 wt % of subsequent dissolution of the contents for next 120 minutes in the second solution (pH 6.8), according to the paddle method of the dissolution test in the Korean pharmacopoeia 10th Edition.

The present invention can be explained in detail as follows.

Generally, the cellulose capsule can be prepared to fill and insert the hygroscopic and/or moisture sensitive preparation due to its lower water content (less than 7 wt %). Also, it can be useful to avoid the protein denaturalization and bovine spongiform encephalopathy (BSE) incurred in gelatin.

However, the cellulose capsule also has the handicaps of its physical properties, such as, low film strength, low film plasticity and/or low storage stability of cellulose film, which are caused by insufficient gelation in the course of solubilizing cellulose.

For improving the gelling property as well as film strength of cellulose capsule, the inventor of present invention has developed a cellulose capsule having optimal combination of gelling agent and auxiliary gelling agent, which results in the improvement of bioavailability.

For this purpose, the inventor of present invention has prepared a cellulose capsule after selecting amid pectin and iota-carrageenan as a gelling agent, potassium carbonate and calcium gluconate as an auxiliary gelling agent. Further, other additives including a pH neutralizing agent, an emulsifying agent, a viscosity stabilizing agent and a plasticizing agent are selected for improving gelling property and film strength with improved bioavailability.

The amount of amid pectin as gelling agent is 2.0-4.0 wt part, preferably 2.5-3.5 wt part as to 100 wt part of aqueous solution of solubilized cellulose, while the amount of iota-carrageenan is 0.1-1.0 wt part, preferably 0.3-0.8 wt part of aqueous solution of solubilized cellulose.

On the other hand, the amount of potassium carbonate is 0.01-0.2 wt part and the amount of calcium gluconate is 0.01-0.2 wt part as auxiliary gelling agent.

Pectin is a hydrocolloidal compound used for a thickening agent, a jellifying agent or a texturizer in food processing, which consists of methylester of polygalacturonic acid bound to hemi-cellulose or α-cellulose. Of course, pectin can be classified according to the degree of methyl esterification (DE) of carboxyl group, which influence the properties of pectin, especially the solubility and gel formation.

Pectin used in the present invention is low methoxyl amide pectin.

Further, 0.01-0.1 wt part of a colloidal silica as viscosity stabilizing agent is introduced for stabilizing the viscosity of cellulose film.

This colloidal silica used in the present invention has been prepared from sodium silicate or water glass as raw material using ion exchange method or acid polymerization method. This colloidal silica is stable spherical particle having 5-8 wt % of $SiO_2$ content, pH 10-12 with 2-5 nm of particle size.

Further, for improving the film strength of cellulose capsule, a plasticizing agent is required. The materials for plasticizing agent can be glycerin, PEG 4000 and/or propylene glycol. PEG 4000 is preferred as a plasticizing agent. the amount of plasticizing agent is 0.01-0.1 wt part, preferably 0.02-0.1 wt part.

The acid resistant cellulose capsule of the present invention can include an emulsifying agent. 0.01-0.2 wt part of sucrose fatty acid ester and diacetylated monoglyceride can be included as an emulsifying agent.

Further, the acid resistant cellulose capsule of the present invention can include 0.01-0.1 wt part, preferably 0.02-0.05 wt part of glacial acetic acid as pH neutralizing agent.

An acid resistant cellulose capsule prepared by the method of present invention has a dissolution profile showing 8-12 wt % of dissolution of the contents for 120 minutes in the first solution (pH 1.2) and 95-100 wt % of subsequent dissolution of the contents for next 120 minutes in the second solution (pH 6.8), according to the paddle method of the dissolution test in the Korean pharmacopoeia 10th Edition.

Further, an acid resistant cellulose capsule prepared by the method of present invention has a bioavailability of ingredient drug showing at least 5% increase of Area Under Curve (AUC) compared to that of currently marketed cellulose capsule.

The increase of bioavailability of ingredient drug filled in cellulose capsule of the present invention can be estimated due to the acid resistant property according to the increase of amid pectin as gelling agent and the delay of dissolution and disintegration of cellulose capsule in the gastrointestinal track.

Further, it also can be estimated that the potassium carbonate as an auxiliary gelling agent can influence the delay of dissolution and disintegration of cellulose capsule in the gastrointestinal track. Therefore, the ingredient drug can have a sustained release property according to the delay of absorption of ingredient drug, which increase the bioavailability.

The process for manufacturing an acid resistant cellulose capsule of the present invention can comprise 2-step processes as follows.

(Step 1) Preparation of Solubilized Aqueous Cellulose Composition

In this step, 100 wt part of aqueous solution of solubilized cellulose including 15-25 wt part of cellulose has been prepared. In the next step, a mixture of 2.0-4.0 wt part of amide pectin and 0.1-1.0 wt part of iota-carrageenan as a gelling agent, 0.01-0.2 wt part of potassium carbonate and 0.01-0.2 wt part of calcium gluconate as an auxiliary gelling agent have been added and stirred to the aqueous solution of solubilized cellulose. Sequentially, 0.01-0.1 wt part of glacial acetic acid as a pH neutralizing agent, 0.01-0.2 wt part of sucrose fatty acid ester and diacetylated monoglyceride as an emulsifying agent, 0.01-0.1 wt part of colloidal silica as a viscosity stabilizing agent and 0.01-0.1 wt part of glycerin, PEG 4000 and/or propylene glycol as a plasticizing agent have been added and stirred to the resulting admixture.

An aqueous solution of solubilized cellulose has been heated until 80-90° C., which is about the gelling temperature of cellulose. Subsequently, a gelling agent and an auxiliary gelling agent have been added and stirred. Sequentially, a pH neutralizing agent, an emulsifying agent, a viscosity stabilizing agent and a plasticizing agent have been also added and stirred. Subsequently, the temperature of mixture has been cooled until 38-43° C.

(Step 2) Formation of Acid Resistant Cellulose Capsule

In this step, a solubilized cellulose mixture obtained in Step 1 has been allowed to stand still and to be equilibrated with adjusting its viscosity. Further, the bubble can be removed by equilibrating the cellulose mixture. After heating the cellulose mixture until 60° C., cellulose capsule has been formed using molding pin. Finally an acid resistant cellulose capsule can be manufactured after drying it at 30-37° C.

The present invention can be explained more concretely by following Preparation Example, Comparative Preparation Examples and Examples. However, it should be understood that the Examples are intended to illustrate but not in any manner to limit the scope of the present invention.

Preparation Example

Preparation of Acid Resistant Cellulose Capsule of the Present Invention 1000 g of aqueous solution of solubilized cellulose has been obtained after dissolving 200 g of cellulose in 0.8 L of purified water heated until 90° C. Subsequently, 28 g of amide pectin and 6 g of iota-carrageenan as a gelling agent, 0.75 g of potassium carbonate and 0.75 g of calcium gluconate as an auxiliary gelling agent, 0.2 g of glacial acetic acid as a pH neutralizing agent, 0.5 g of sucrose fatty acid ester and 0.02 g of diacetylated monoglyceride as an emulsifying agent, 0.3 g of colloidal silica as a viscosity stabilizing agent, 0.1 g of glycerin, 0.5 g of PEG 4000 and 0.5 g of propylene glycol as a plasticizing agent have been added and stirred to the resulting admixture. A solubilized cellulose mixture has been obtained after cooling it slowly until 40° C. Then, obtained cellulose mixture allowed to stand still and to be equilibrated with adjusting its viscosity. After heating the cellulose mixture until 60° C., cellulose capsule has been formed using molding pin. Finally, an acid resistant cellulose capsule can be manufactured after drying it.

Comparative Preparation Example 1

Preparation of Acid Resistant Cellulose Capsule Disclosed in WO 2011/36601

1000 g of aqueous solution of solubilized cellulose has been obtained after dissolving 200 g of cellulose in 0.8 L of purified water heated until 75° C. Subsequently, 28 g of gellan gum as a gelling agent, 0.5 g of sucrose fatty acid ester as an emulsifying agent have been added and stirred to the resulting admixture. A solubilized cellulose mixture has been obtained after cooling it slowly until 45° C. Then, obtained cellulose mixture allowed to stand still and to be equilibrated with adjusting its viscosity. After heating the cellulose mixture until 60° C., cellulose capsule has been formed using molding pin. Finally, an acid resistant cellulose capsule can be manufactured after drying it.

The cellulose capsule prepared in Comparative Preparation Example 1 do not include an auxiliary gelling agent, an pH neutralizing agent, a viscosity stabilizing agent and a plasticizing agent in the cellulose capsule.

Comparative Preparation Example 2

Preparation of Acid Resistant Cellulose Capsule (Excluding a Viscosity Stabilizing Agent and a Plasticizing Agent)

1000 g of aqueous solution of solubilized cellulose has been obtained after dissolving 200 g of cellulose in 0.8 L of purified water heated until 75° C. Subsequently, 28 g of amide pectin and 6 g of iota-carrageenan as a gelling agent, 0.75 g of potassium carbonate and 0.75 g of calcium gluconate as an auxiliary gelling agent, 0.2 g of glacial acetic acid as a pH neutralizing agent, 0.5 g of sucrose fatty acid ester and 0.02 g of diacetylated monoglyceride as an emulsifying agent have been added and stirred to the resulting admixture. A solubilized cellulose mixture has been obtained after cooling it slowly until 40° C. Then, obtained cellulose mixture allowed to stand still and to be equilibrated with adjusting its viscosity. After heating the cellulose mixture until 60° C., cellulose capsule has been formed using molding pin. Finally, an acid resistant cellulose capsule can be manufactured after drying it.

Comparative Preparation Example 3

Preparation of Commercially Marketed EMBO Capsule VG$^{NS}$ by Suheung 1000 g of aqueous solution of solubilized cellulose has been obtained after dissolving 200 g of cellulose in 0.8 L of purified water heated until 75° C. Subsequently, 6 g of amide pectin as a gelling agent, 0.5 g of calcium gluconate as an auxiliary gelling agent, 0.2 g of glacial acetic acid as a pH neutralizing agent, 0.5 g of sucrose fatty acid ester as an emulsifying agent, 0.1 g of glycerin as a plasticizing agent have been added and stirred to the resulting admixture. A solubilized cellulose mixture has been obtained after cooling it slowly until 40° C. Then, obtained cellulose mixture allowed to stand still and to be equilibrated with adjusting its viscosity. After heating the cellulose mixture until 60° C., cellulose capsule has been formed using molding pin. Finally, an acid resistant cellulose capsule can be manufactured after drying it.

(Example 1) Film Strength Test

The film strength of cellulose capsule has been measured using the #0 size cellulose capsules prepared in Preparation Example and Comparative Preparation Examples 1-3. Texture Analyser (Model TA 1000) has been used for measuring a mechanical film strength. The speed of dropping down hammer has been 0.5 mm/sec and the mechanical film strength has been measured at 4 mm pressing depth under the surface of capsule. The result has been shown in Table 1.

TABLE 1

| | | Prep. Example | Comp. Prep. Example 1 | Comp. Prep. Example 2 | Comp. Prep. Example 3 |
|---|---|---|---|---|---|
| Film strength | Max. | 466 | 417 | 422 | 451 |
| | Average | 422 | 382 | 387 | 408 |
| | Min. | 385 | 369 | 360 | 369 |

(Unit: g/cm$^2$)

The film strength of acid resistant cellulose capsule prepared by Preparation Example is 422 g/cm$^2$. On the other hand, the film strength of capsules prepared by Comparative Preparation Example 1 and 2 shows 382 g/cm$^2$ and 387 g/cm$^2$ respectively. Since cellulose capsules prepared in Comparative Preparation Example 1 and 2 have not included both viscosity stabilizing agent and plasticizing agent in the cellulose capsule, it seems that the film strength of cellulose capsule may be declined.

On the other hand, the film strength of a cellulose capsule prepared in Comparative Preparation Example 3 which is a commercially marketed EMBO capsule VG$^{NS}$ by Suheung shows slightly lower than that of Preparation Example in the present invention.

Therefore, the cellulose capsule of the present invention shows better film strength compared to that of commercially marketed capsule. It can be estimated that the increase of film strength of the cellulose capsule of the present invention can be resulted from the addition of potassium carbonate and calcium gluconate as an auxiliary gelling agent, colloidal silica as a viscosity stabilizing agent and/or PEG 4000 and PG as plasticizing agent in the cellulose composition.

(Example 2) Dissolution Test

After acetaminophen has been filled in sample capsules, dissolution test has been carried out according to the paddle method of the dissolution test in the Korean pharmacopoeia 10th Edition. A transparent and colorless first solution (pH 1.2) has been prepared, after 7.0 ml of hydrochloric acid and 2.0 g of sodium chloride have been dissolved to make 1000 ml. Further, second solution (pH 6.8) has been prepared by mixing pH 6.8 phosphate buffer and purified water (1:1). The temperature of each solution has been at 37.5° C.±0.5° C. The rotation of paddle has been 50 rpm and the test material for detecting dissolution has been collected at 0, 30, 60, 90, 120, 150, 180, 210 and 240 minutes. The amount of dissolved acetaminophen has been measured by HPLC method.

Further, FIG. 1 shows a dissolution profile of acetaminophen by an acid resistant cellulose capsule of the present invention (Preparation Exp) and an acid resistant cellulose capsule EMBO CAPS VGNS manufactured and marketed by Suheung Co., Ltd. (Comparative Preparation Exp 3), according to the paddle method of the dissolution test in the Korean pharmacopoeia 10th Edition.

Table 2 shows the acetaminophen dissolution profile for 120 minutes at the first solution and subsequently for 120 minutes at the second solution.

TABLE 2

| | Time (min.) | | | | | | | | |
|---|---|---|---|---|---|---|---|---|---|
| | 0 | 30 | 60 | 90 | 120 | 150 | 180 | 210 | 240 |
| Prep. Example | 0 | 3 | 6 | 8 | 12 | 95 | 98 | 99 | 100 |
| Comp. Prep. Example 1 | 0 | 3 | 7 | 10 | 14 | 92 | 94 | 98 | 99 |
| Comp. Prep. Example 3 | 0 | 24 | 67 | 88 | 95 | 97 | 99 | 99 | 100 |

(Unit: wt %)

The dissolution profile shows that acid resistant cellulose capsule prepared in Preparation Example of present invention has been similar to that of acid resistant cellulose capsule prepared according to the method of WO 2011/36601 (Comparative Preparation Exp 1). However, the dissolution profile of cellulose capsule EMBO CAPS VGNS manufactured and marketed by Suheung Co., Ltd. (Comparative Preparation Exp 3) cannot show the characteristics of enteric formulation.

The enteric properties of dissolution profile of Preparation Example of present invention can be estimated by the result of 5 times increasing amount of amide pectin compared from that of marketed cellulose capsule EMBO CAPS VGNS manufactured by Suheung Co., Ltd. in Comparative Preparation Example 3.

(Example 3) Bioavailability Test

Cellulose capsule prepared in Preparation Example of the present invention and cellulose capsule prepared in Comparative Preparation Example 3, EMBO Capsule VG commercially marketed by Suheung Co., Ltd. have been used for bioavailability test after filling acetaminophen. The bioavailability test has been measured by the plasma concentration of acetaminophen in test animal of Beagles according to lapse of time.

Figure 2:
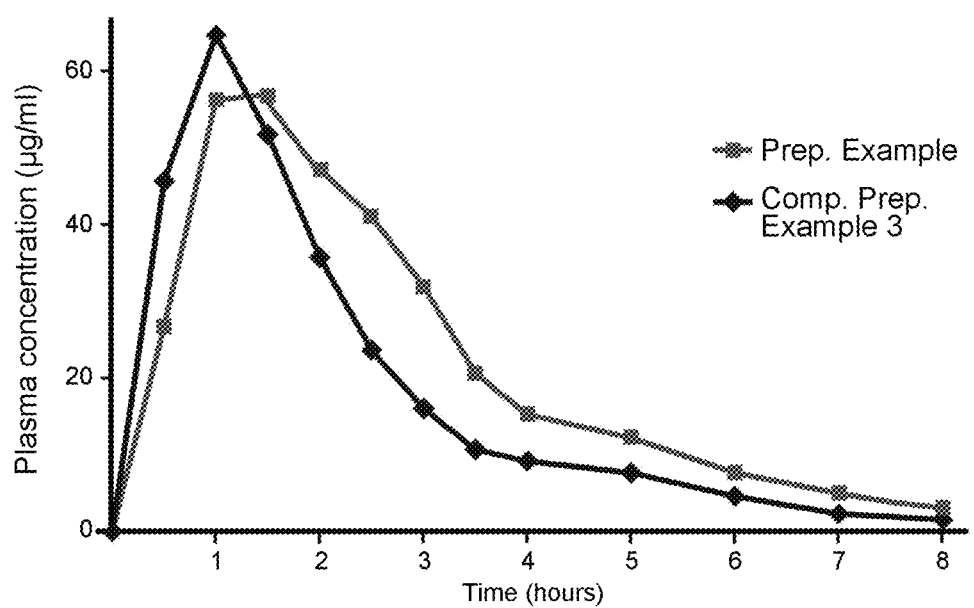
FIG. 2 shows a graph showing the change of plasma concentration of acetaminophen according to lapse of time, when acetaminophen is filled and administered to Beagles in both the acid resistant cellulose capsule of the present invention, and the cellulose capsule EMBO CAPS VG commercially marketed by Suheung Co., Ltd.

6 animals have been divided into 2 groups and each group has 3 test animals. Each 250 mg of acetaminophen has been filled into the hard capsules prepared in Preparation Example and Comparative Preparation Example 3, and hard capsules have been orally administered to the test animals of Beagles. For evaluating the bioavailability, the plasma concentrations of acetaminophen in test animals have been measured by every hour for 8 hours. The pharmacokinetic parameters have been analyzed. The results are shown in FIG. 2 and Table 3.

FIG. 3 is a graph showing the changes of plasma concentrations of acetaminophen according to the lapse of time, when the acetaminophen is filled and administered to the Beagles in both cellulose capsule of the present invention and cellulose capsule prepared in Comparative Preparation Example 3, that is, EMBO CAPS VG capsule commercially marketed by Suheung Co., Ltd.

TABLE 3

| Pharmacokinetic parameters | | |
|---|---|---|
| | Prep. Ex. | Com. Pre. Ex. 3 |
| AUC (µg · hr/ml) | 132.3 | 125.2 |
| $C_{max}$ (µg/ml) | 58.4 | 64.3 |
| $T_{max}$ (hour) | 1.24 | 0.91 |

The cellulose capsule prepared in Preparation Example of the present invention has shown the better bioavailability compared to that of cellulose hard capsule prepared in Comparative Preparation Example 3, EMBO Capsule VG commercially marketed by Suheung Co., Ltd.

In detail, the value of the maximum plasma concentration ($C_{max}$) of cellulose capsule prepared in Comparative Preparation Example 3, EMBO Capsule VG is slightly higher than that of cellulose capsule of the present invention.

On the other hand, the time required for maximum plasma concentration ($T_{max}$) has a difference, that are 1.24 hour vs 0.91 hour. According to the bioavailability evaluating value of AUC (Area Under Curve), the AUC value of cellulose capsule prepared in Preparation Example of the present invention increases at least 5.0% compared to that of cellulose hard capsule prepared in Comparative Preparation Example 3, EMBO Capsule VG commercially marketed by Suheung Co., Ltd.

Therefore, it has been confirmed that cellulose capsule of the present invention shows the better bioavailability of ingredient, by at least 5% increase of AUC value compared to that of commercially available cellulose capsule using a chemical gelling agent.

The invention claimed is:

1. A process for preparing an acid resistant cellulose capsule, the process comprising:
   i) preparing 100 wt part of aqueous solution of solubilized cellulose including 15-25 wt part of cellulose;
   ii) adding and stirring 2.0-4.0 wt part of amide pectin and 0.1-1.0 wt part of iota-carrageenan as a gelling agent, and 0.01-0.2 wt part of potassium carbonate and 0.01-0.2 wt part of calcium gluconate as an auxiliary gelling agent to the aqueous solution of solubilized cellulose;
   iii) sequentially adding and stirring 0.01-0.1 wt part of glacial acetic acid as a pH neutralizing agent, 0.01-0.2 wt part of sucrose fatty acid ester and diacetylated monoglyceride as an emulsifying agent, 0.01-0.1 wt part of colloidal silica as a viscosity stabilizing agent, and 0.01-0.1 wt part of glycerin, PEG 4000 and/or propylene glycol as a plasticizing agent to the resulting admixture to create an obtained product;
   iv) allowing the obtained product to stand and to be equilibrated; and
   v) forming and drying a cellulose capsule.

2. The process for preparing an acid resistant cellulose capsule according to claim 1, wherein in said step iv), the obtained product stands at 65° C.; and
   wherein forming and drying a cellulose capsule comprises: dipping a molding pin for forming the cellulose capsule, and drying the cellulose capsule at 30-37° C.

3. The process for preparing an acid resistant cellulose capsule according to claim 1, wherein said amide pectin is low methoxyl amide pectin.

4. The process for preparing an acid resistant cellulose capsule according to claim 1, wherein said colloidal silica is stable spherical particles having 5-8 wt % of $SiO_2$ content, a pH of 10-12 and a particle size of 2-5 nm.

5. An acid resistant cellulose capsule prepared by the method of claim 1.

6. An acid resistant cellulose capsule prepared by the method of claim 1, wherein the dissolution profile shows 8-12 wt % of dissolution of the contents for an initial 120 minutes in a first solution having a pH of 1.2 and 95-100 wt % of subsequent dissolution of the contents for the next 120 minutes in a second solution having a pH of 6.8, according to the paddle method of the dissolution test in the Korean pharmacopoeia 10th Edition.

* * * * *